US010406337B2

(12) United States Patent
Locke et al.

(10) Patent No.: US 10,406,337 B2
(45) Date of Patent: Sep. 10, 2019

(54) SYSTEMS AND METHODS OF STIMULATION AND ACTIVATION OF FLUIDS FOR USE WITH INSTILLATION THERAPY

(71) Applicant: KCI Licensing, Inc., San Antonio, TX (US)

(72) Inventors: Christopher Brian Locke, Bournemouth (GB); Timothy Mark Robinson, Shillingstone (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 374 days.

(21) Appl. No.: 15/456,886

(22) Filed: Mar. 13, 2017

(65) Prior Publication Data

US 2017/0239096 A1 Aug. 24, 2017

Related U.S. Application Data

(63) Continuation of application No. 14/216,522, filed on Mar. 17, 2014, now Pat. No. 9,623,224, which is a (Continued)

(51) Int. Cl.
*A61M 35/00* (2006.01)
*A61M 1/00* (2006.01)
*A61N 5/06* (2006.01)
*A61N 5/02* (2006.01)
*A61F 13/00* (2006.01)
(Continued)

(52) U.S. Cl.
CPC ....... *A61M 35/00* (2013.01); *A61F 13/00068* (2013.01); *A61K 41/0047* (2013.01); *A61L 15/18* (2013.01); *A61L 15/44* (2013.01); *A61L 15/64* (2013.01); *A61M 1/0058* (2013.01); *A61M 1/0084* (2013.01); *A61M 1/0088* (2013.01); *A61N 5/02* (2013.01); *A61N 5/062* (2013.01); *A61K 41/00* (2013.01);
(Continued)

(58) Field of Classification Search
CPC .............. A61M 1/0058; A61M 1/0084; A61M 1/0088; A61M 35/00; A61K 41/00; A61N 5/02; A61N 5/062; A61F 13/00068
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Benjamin J Klein

(57) ABSTRACT

Systems and methods of stimulating or activating fluids for use in wound treatment systems.

26 Claims, 2 Drawing Sheets

Related U.S. Application Data continuation of application No. 13/477,741, filed on May 22, 2012, now Pat. No. 8,708,981.

(60) Provisional application No. 61/490,150, filed on May 26, 2011.

(51) Int. Cl.
*A61K 41/00* (2006.01)
*A61L 15/18* (2006.01)
*A61L 15/44* (2006.01)
*A61L 15/64* (2006.01)

(52) U.S. Cl.
CPC .......... *A61L 2300/418* (2013.01); *A61M 2202/0241* (2013.01); *A61M 2202/0468* (2013.01)

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,944,067 B2 * | 2/2015 | Robinson .......... A61F 13/00063 128/849 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0034904 A1 * | 2/2006 | Weimann ............ A61K 9/0009 424/449 |
| 2006/0073207 A1 * | 4/2006 | Masters ............... A61K 8/64 424/488 |
| 2006/0173514 A1 | 8/2006 | Biel et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 A | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |

(56) References Cited

FOREIGN PATENT DOCUMENTS

| WO | 96/05873 A1 | 2/1996 |
|---|---|---|
| WO | 97/18007 A1 | 5/1997 |
| WO | 99/13793 A1 | 3/1999 |
| WO | 2005105180 A1 | 11/2005 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
First Examination Report corresponding to Australian Application No. 2016228240 dated Jul. 20, 2017.

* cited by examiner

SYSTEMS AND METHODS OF STIMULATION AND ACTIVATION OF FLUIDS FOR USE WITH INSTILLATION THERAPY

CROSS-REFERENCE TO RELATED APPLICATIONS

This application is a continuation of U.S. patent application Ser. No. 14/216,522, filed Mar. 17, 2014, which claims priority to U.S. patent application Ser. No. 13/477,741, filed May 22, 2012, which is now U.S. Pat. No. 8,708,981, issued Apr. 29, 2014, which claims priority to U.S. Provisional Patent Application Ser. No. 61/490,150, filed May 26, 2011, the entire contents of which are incorporated herein by reference.

BACKGROUND

1. Field of the Invention

The present invention relates generally to healing of wounds and wound-treatment therapies. More particularly, but not by way of limitation, the present invention relates to fluid-instillation and negative-pressure wound therapies.

2. Background Information

Clinical studies and practice have shown that providing therapeutic fluids, particularly in conjunction with reduced pressure, in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape). Instillation fluids may be delivered to the wound insert and held in place at the site of the wound, further improving the efficacy of treatment.

Wound treatment systems, including for example, instillation therapy units such as the V.A.C. Ulta Therapy System, available from Kinetic Concepts, Inc., San Antonio, Tex. U.S.A. may be used to deliver fluids with a more pronounced therapeutic benefit than saline, and indeed, may expand in complexity and capability to be able to deliver a plurality of fluids for different purposes dependent upon wound conditions. It is believed that fluids will be able to be used to reduce infection, to aid with debridement, to improve the dressings removability and to address biofilm buildup in the wound.

Certain systems offer fluids with molecules which are tailored and effective to provide the benefits described the above, but often are not designed for use with a system which doses the fluid over time and exposes the fluid to tubing and other plastic components. For example, wound treatment fluids may contain an active molecule that reacts with various types of plastic and light (including, e.g., ultraviolet light), thus weakening the molecules effectiveness and making its practical delivery to the wound site more difficult.

It is therefore desirable in systems with molecules which may be susceptible to negative impacts of contact with certain materials or light to protect them or render them immune to these range of deleterious effects until the system determines they should be active.

As described herein, it is possible to provide for control of the stimulation or activation of fluids used in wound treatment systems.

SUMMARY

Systems and methods of stimulating or activating fluids for use in wound treatment systems are presented.

Certain embodiments include a wound treatment system comprising: a wound dressing; a fluid storage device comprising a fluid, where the fluid storage device is in fluid communication with the wound dressing; and an energy source configured to direct energy to the fluid and to activate a therapeutic property of the fluid. Particular embodiments further comprise a negative pressure source coupled to the wound dressing. In certain embodiments, the fluid comprises molecules with a coating prior to exposure to the energy source. In particular embodiments, the energy source is configured to degrade the protective coating. In specific embodiments, the energy source is configured to activate a component of the fluid that degrades the protective coating.

In certain embodiments, the protective coating comprises a polymer shell. In particular embodiments, the protective coating comprises a bioabsorbable glass. In specific embodiments, the protective coating comprises a ceramic.

In particular embodiments, the energy source emits ultrasonic energy. In certain embodiments, the energy source emits magnetic energy. In specific embodiments, the energy source emits radio frequency energy. In particular embodiments, the energy source emits ionizing radiation energy. In certain embodiments, the energy source emits microwave energy. In certain embodiments, the energy source emits light energy. In particular embodiments, the energy source is configured to direct energy to the fluid proximal to the wound dressing.

Specific embodiments comprise a conduit in fluid communication with the fluid storage device and the wound dressing. In certain embodiments, the energy source is configured to direct energy to the fluid in the conduit. Particular embodiments comprise a coupling member coupling the conduit to the wound dressing. In certain embodiments, the energy source is configured to direct energy to the coupling member. In specific embodiments, the therapeutic property includes an anti-biotic property. In certain embodiments, the therapeutic property includes an analgesic property. In particular embodiments, the therapeutic property aids with debridement of tissue. In certain embodiments, the therapeutic property improves the ability to remove the wound dressing from a wound. In specific embodiments, the therapeutic property reduces biofilm buildup in a wound.

Particular embodiments include a method of treating a wound, where the method comprises: applying a wound dressing to a wound; transporting fluid to the wound dressing; and directing energy to the fluid and activating a therapeutic property of the fluid. In certain embodiments, the energy is directed to the fluid proximal to the wound dressing. Specific embodiments also include applying a negative pressure to the wound dressing. Particular embodiments also include providing a fluid storage device and a conduit in fluid communication with the wound dressing. In certain embodiments, the energy is directed to the fluid when the fluid is in the conduit. Particular embodiments also include a coupling member coupling the conduit to the wound dressing. In specific embodiments, the energy is directed to the fluid at the coupling member. In certain embodiments, the fluid comprises molecules having a coating and an active agent, and directing energy to the fluid breaks down the protective coating.

Particular embodiments include a wound treatment system comprising: a wound dressing; a negative pressure source coupled to the wound dressing; a fluid storage device comprising a fluid with molecules having a coating, wherein the fluid storage device is configured for fluid communication with the wound dressing; and an energy source configured to direct energy to the fluid and degrade the coating.

In specific embodiments, the energy source directs light energy to the fluid. In certain embodiments, the energy source directs ultrasonic energy to the fluid. In certain embodiments, the energy source directs magnetic energy to the fluid. In particular embodiments, the energy source directs radio frequency energy to the fluid. In certain embodiments, the energy source directs ionizing radiation energy to the fluid. In particular embodiments, a therapeutic property of the fluid is activated when the coating is degraded.

Certain embodiments include a method of treating a wound, where the method comprises: applying a wound dressing to a wound; transporting fluid to the wound dressing, where the fluid comprises molecules having a coating; and directing energy to the fluid and degrading the coating. In specific embodiments, degrading the coating activates a therapeutic property of the fluid. In particular embodiments, the therapeutic property includes an anti-biotic property. In certain embodiments, the therapeutic property includes an analgesic property. In particular embodiments, the therapeutic property aids with debridement of tissue. In certain embodiments, the therapeutic property improves the ability to remove the wound dressing from a wound. In particular embodiments, the therapeutic property reduces biofilm buildup in a wound.

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a wound-treatment method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises one of the present wound inserts and a drape, the wound dressing includes the specified elements but is not limited to having only those elements. For example, such a wound dressing could also include a connection pad configured to be coupled to a negative pressure wound therapy (NPWT) apparatus (e.g., including a vacuum source and/or a fluid source).

Further, a device or structure that is configured in a certain way is configured in at least that way, but it can also be configured in other ways than those specifically described.

Figure 1:
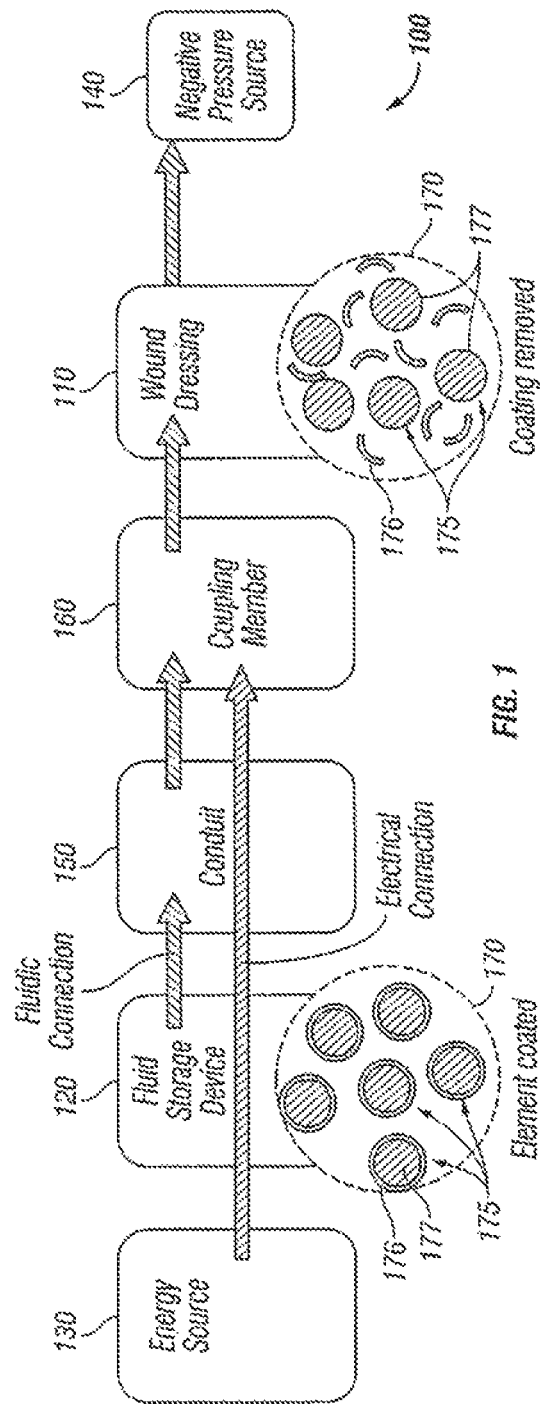
FIG. 1 illustrates a schematic diagram of an embodiment of a wound treatment system.

Turning now to the figures, FIG. 1 depicts a schematic diagram of a wound treatment system 100 comprising a wound dressing 110, a fluid storage device 120, an energy source 130, and a negative pressure source 140. An overview of the operation of wound treatment system 100 will be provided initially, followed by a more detailed discussion of an exemplary embodiment.

In the exemplary embodiment shown in FIG. 1, fluid storage device 120 is in fluid communication with wound dressing 110 via a conduit 150. In addition, energy source 130 is coupled to a coupling member 160, which is in turn coupled to wound dressing 110.

In this exemplary embodiment, fluid storage device 120 comprises a fluid 170 with molecules 175 having a protective coating 176 around an active agent 177. During operation, fluid 170 is transported from fluid storage device 120, through conduit 150 and coupling member 160 to wound dressing 110. In the embodiment shown, energy source 130 can be activated to direct energy towards fluid 170 at coupling member 160. The exposure of fluid 170 to energy emitted from energy source 130 can degrade or break down protective coating 176 and allow active agent 177 to be exposed, thereby activating a therapeutic property of fluid 170. Negative pressure source 140 can then draw fluid 170 from wound dressing 110 into a suitable storage container (not shown).

Figure 2:
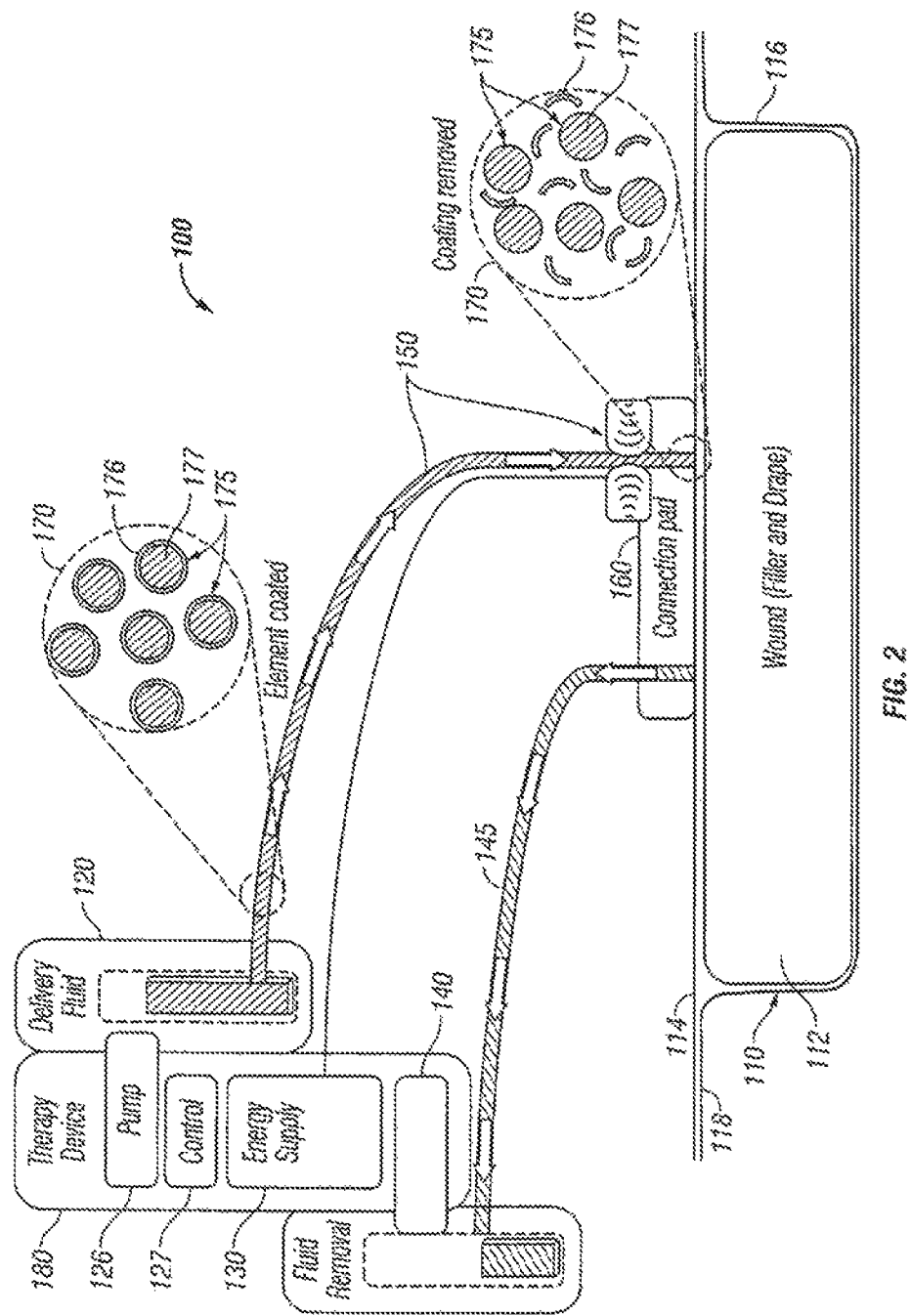
FIG. 2 illustrates a schematic view of the embodiment of FIG. 1.

Referring now to FIG. 2, a more detailed view and discussion of wound treatment system 100 is provided. In this embodiment, fluid storage device 120 and energy source 130 are housed in wound treatment apparatus 180, along with a supply pump 126 and a control system 127. As previously explained, fluid storage device comprises fluid 170 having molecules 175 with protective coating 176 around active agent 177. In this embodiment, control system 127 is used to control supply pump 126, which pumps fluid 170 to wound dressing 110. It is understood that in other exemplary embodiments, negative pressure source 140 may be used to draw fluid from fluid storage device 120 without the use of supply pump 126.

In this embodiment wound dressing 110 comprises a wound insert 112, which is shown placed in wound 116 of a patient (not shown). A drape 114 is placed over wound 116 and wound insert 112 such that wound insert 112 is between drape 114 and wound 116. In the illustrated embodiment, drape 114 is coupled to the skin 118 of the patient. In this exemplary embodiment, wound insert 112 is coupled to a fluid storage device 120 by conduit 150. Wound treatment apparatus 180 may also comprise negative pressure source 140 configured to apply negative pressure to wound insert 112 through a conduit 145 or conduit 150 (if the conduit is a multi-lumen conduit as further explained below).

Wound insert 112 may be a foam member, which may be open-celled and/or reticulated. In specific embodiments, the wound insert comprises an open-celled reticulated foam. An open-celled reticulated foam has a netlike microstructure, with few if any closed cells. In certain embodiments, the porosity can range from 95%-98%, though less porous or more porous foams may be used.

In certain embodiments, wound insert 112 may comprise a polyurethane, such as polyurethane-polyester or polyurethane-polyether; polyolefins, such as polypropylenes (PP) or polyethylenes (PE); silicone polymers; polyvinylchloride; polyamides; polyesters; acrylics; thermoplastic elastomers such as styrene-butene-styrene (SBS) or styrene-ethylene-butene-styrene (SEBS); polyether-amide block copolymers (PEBAX); elastomers such as styrene butadiene rubber (SBR); ethylene propylene rubber (EPR); ethylene propylene diene modified rubber (EPDM); natural rubber (NR); ethylene vinyl acetate (EVA); polyvinyl alcohol (PVOH); polyvinyl acetal; or polyvinyl butyral (PVB). Additionally, wound insert 20 may comprise a bioabsorbable polymer, examples of which include polylactic acid, polylactide (PLA), polyglycolic acid, polyglycolide (PGA), and polycaprolactone (PCL). Methods of manufacturing open-celled reticulated foam are well known. Open-celled reticulated foam is commercially available from a variety of sources, including Kinetic Concepts, Inc., San Antonio, Tex., U.S.A. (www.kci1.com).

Wound insert 112 may be of any suitable shape having a depth dimension, including a sheet, a rectangular prism, a cone, a cylinder, a sphere, or any other suitable shape.

In the exemplary embodiment shown, wound treatment apparatus 180 comprises a fluid storage device 120 configured to deliver fluid 170 through conduit 150 to wound dressing 110. In certain exemplary embodiments, fluid 170 may comprise medicinal fluids, antibacterial fluids, or irrigation fluids.

In specific exemplary embodiments, conduit 150 may comprise a single lumen conduit (e.g., switched between a vacuum source and/or a fluid source) or can comprise multiple single-lumen conduits or a multi-lumen conduit such that, for example, fluid can be delivered and/or negative pressure can be applied to wound dressing 110 individually or simultaneously. In other exemplary embodiments conduit 150 can comprise multiple lumens, for example, as in a single conduit with a central lumen for application of negative pressure and/or fluid delivery and one or more peripheral lumens disposed adjacent or around the central lumen such that the peripheral lumens can be coupled to a pressure sensor to sense and/or detect a pressure or negative pressure between drape 114 and a wound surface. In the embodiment shown, system 100 further comprises a coupling member 160 configured to be coupled to conduit 150. One example of a suitable coupling member 160 is the "V.A.C. T.R.A.C.® Pad," commercially available from KCI USA, Inc. of San Antonio, Tex., U.S.A. One example of a suitable drape 114 includes the "V.A.C.® Drape" commercially available from Kinetic Concepts, Inc., San Antonio, Tex., U.S.A (www.kci1.com). Various wound therapy systems and components are commercially available through Kinetic Concepts, Inc. and its affiliates.

In the embodiment shown in FIG. 2, wound treatment apparatus 180 may be configured to deliver instillation fluid to wound 116, to remove fluid from wound 116, and to apply negative pressure to wound 116 through drape 114 and wound insert 112.

Wound treatment apparatus 180 may be activated to deliver fluid 170 from fluid storage device 120 to wound 116 through conduit 150 coupled to wound insert 112 through coupling member 160. Negative pressure source 140 may also be actuated to provide negative pressure to wound 116 through drape 114 and wound insert 112.

Example of fluids 170 that may be delivered to wound 116 include hypochlorous acid (HOCl) and hypochlorite ion (ClO⁻, which is also commonly referred to, generally understood to be synonymous with, and may be referred to interchangeably in this disclosure as, OCl⁻), which are examples of effective antimicrobial agents for biocidal action. For example, HOCl is typically capable of killing a broad spectrum of microbes (e.g., fungus, bacteria, viruses, fungus, yeast, and the like); often in a relatively short period of time (e.g., is capable of killing greater than 99% of microbes within a period of less than 10 seconds).

Such antimicrobial agents can be generated or formed by a combination of the present reactive agents and fluid (e.g., water and/or aqueous solution, such as, for example, saline solution) and may be more effective and/or more versatile than antibiotics and other commonly used antimicrobial agents used in wound treatment in the past. For example, antibiotics may be bacteria-specific such that testing may be required to determine a suitable antibiotic to use for a specific wound or infection; and/or such that antibiotics may have only limited effectiveness for individual wounds and/or infections (e.g., where testing is not performed and/or where a wound is infected with a plurality of different bacteria).

Such testing may take as long as several days to determine an appropriate antibiotic, delaying treatment or selection of an effective antibiotic. Additionally, bacteria may develop resistance to antibiotics, such that antibiotics may have reduced effectiveness after an amount of time. Further, antibiotics are typically administered intravenously (systemically) such that antibiotics may kill beneficial bacteria (e.g., in a patient's digestive system) and/or may cause organ damage (e.g., to a patient's liver).

Further, wound treatment apparatus 180 may be configured to remove spent instillation fluids, secretions, and/or infected tissue from wound 116. Undesirable effluent may be removed by actuating the negative pressure source 140; effluent may flow into wound insert, through conduit 145, and into a waste chamber coupled to wound treatment apparatus 180.

As previously described, in this exemplary embodiment, fluid 170 comprises molecules 175 having a protective coating 176 surrounding an active agent 177. In certain embodiments, protective coating 176 may be constructed using a layer-by-layer technique (LbL) where polyallylamine hydrochloride (PAH)/polysodium 4-styrenesulfonate (PSS) may be the layers used to form coating.

During operation, as fluid 170 is initially transported from fluid storage device 120 and through conduit 150, protective coating 176 surrounds active agent 177 of molecules 175. Upon reaching coupling member 160, energy source 130 directs energy to fluid 170 and degrades or breaks down protective coating 176. It is understood that in other embodiments, energy source 130 may direct energy to fluid 150 at other locations within wound treatment system 100. For example energy source 130 may direct energy to fluid 170 at a location within wound treatment apparatus 180, along conduit 150, or directly in wound dressing 110.

In certain embodiments, it may be beneficial to have energy source 130 direct energy to fluid 170 in a location proximal to wound dressing 110. Such a configuration can allow protective coating 176 to remain in place as fluid 170 is transported to wound dressing 110. This can minimize the effects of exposure of fluid 170 to materials or environmental conditions (e.g., light, temperature, etc.) that may affect active agent 177 of fluid 170.

In certain embodiments, energy source 130 may direct ultrasonic, magnetic, radio, ionizing radiation, microwave or light energy to fluid 170. In specific embodiments, energy source 130 may direct ultraviolet, infrared or visible light waves to fluid 170. In certain embodiments, energy source 130 may emit light with a wavelength in the range of approximately 400 nm-450 nm. In particular embodiments, energy source 130 may emit ionizing radiation in the form of gamma rays, x-rays, or electron-beams.

In particular embodiments, energy source 130 may activate a component of fluid 170 that in turn degrades or breaks down protective coating 176. For example, fluid 170 may comprise a component that does not degrade protective coating under particular temperature or light conditions. However, when energy source 130 directs energy to fluid 170, the environmental conditions are changed sufficiently that the component degrades protective coating 176. In other embodiments, energy source 130 may be configured to directly degrade protective coating 176 without the use of an additional component in fluid 170.

After protective coating 176 is degraded, active agent 177 can provide a therapeutic benefit to the patient. Non-limiting examples of the therapeutic benefits that may be provided to a patient include antibiotic and analgesic properties. Therapeutic properties may also aid with debridement, improve the ability to remove the wound dressing, and reduce biofilm buildup in the wound.

By protecting active agent 177 in protective coating 176 until fluid 170 is proximal to wound dressing 110, it is believed that more accurate dosing of active agent 177 can be achieved. For example, in certain prior art wound treatment systems that do not provide for protection of an active ingredient, it may be necessary to increase the dosage or concentrations levels of the active ingredient in a fluid container to account for degradation during delivery. Wound treatment system 100 can reduce the amount of degradation of active agent 177 during transport of fluid 170 throughout.

The various illustrative embodiments of devices, systems, and methods described herein are not intended to be limited to the particular forms disclosed. Rather, they include all modifications and alternatives falling within the scope of the claims. For example, in certain exemplary embodiments, the protective coating may comprise an ultraviolet-activated protective cover which is partially activated to break down by ambient light while traveling through the conduit to the wound dressing (or during storage in the fluid storage device). The breakdown of the protective coating can then be completed by an energy source proximal to the wound dressing.

In certain exemplary embodiments, rather than a protective coating, the fluid may comprise molecules constructed so that the active agent is inhibited by a light sensitive branch. In such embodiments, for example, exposure to ultraviolet light could be used to break the branch and activate the compound. Such configurations could be of use with active agents that have a short active life due to a spontaneous reaction or from interaction with the surrounding environment. In particular embodiments, photoinhibition could also be used to control the behavior of the active agents.

Certain exemplary embodiments may also comprise a clotting agent, e.g. fibrin, chitosan, and trivalent salts, such as $Fe^{+++}$ & $Al^{+++}$. In particular embodiments, a $Fe^{+++}$ compound (such as ferric chloride) can be encapsulated in a glucose sensitive microcapsule (e.g., glutaraldehyde cross-linked hemoglobin and glucose oxidase). On encountering glucose (which may be present in wound fluid or instilled by the user), the permeability of the microcapsule increases allowing for the release of the $Fe^{+++}$ agent. The wound fluid may also enter the microcapsule and initiate the clotting reaction. In specific embodiments, the clotting agent may be applied to the wound dressing. The clotting agent may be protected by an active layer capable of being activated by haemoglobin and releasing the clotting agent locally. In certain embodiments, the clotting agent is the active agent in a molecule with a protective coating, and may be activated as described in previous exemplary embodiments.

In particular embodiments, thrombin may be utilized in the clotting mechanism, for example, in combination with fibrinogen. In specific embodiments, thrombin may be inhibited or 'blocked' by p-Amidinophenyl-(E)-4-diethyl-amino-2-hydroxy-alpha-methylcinnamate hydrochloride through covalent bonding. By exposing the blocked thrombin to light (e.g., at approximately 366 nm) the thrombin may be unblocked and clotting can occur.

In other exemplary embodiments, the fluid may comprise multiple molecules, particles or agents in the fluid which are activated by different wavelengths of light or frequencies of energy, which could be delivered at the point of entry to the wound or once in the wound to activate them. For example, in certain embodiments a light-activated group (e.g. the thrombin-fibrinogen group described above) could be grafted onto a molecule at one location. At another location on the molecule, a group could be grafted that would liberate cations when exposed to light at a wavelength other than 366 nm. Non-limiting examples of such chemical groups that could be used to liberate cations include (photoacid generators [PAGs]) in the 150 nm-350 nm UV light range are carboranes, and diphenyliodonium nitrate (activated at about 226 nm). A simple alternative, avoiding grafting, would be to mix the two sensitive materials (clotting agent and cationic agent). The cationic agent would be acidic and could aid in debriding In particular exemplary embodiments, local activation of the energy source may be utilized in the wound by either a coating on the wound insert local to a targeted issue such as necrotic tissue or by localised external stimulation. In certain exemplary embodiments, multiple molecules in the wound fluid may be utilized which activate based upon reaction with biomarkers in the wound (e.g., inflammatory response markers).

The claims are not intended to include, and should not be interpreted to include, means-plus- or step-plus-function limitations, unless such a limitation is explicitly recited in a given claim using the phrase(s) "means for" or "step for," respectively.

We claim:
1. A wound treatment system comprising:
   a wound dressing;
   a fluid storage device configured to deliver a fluid to the wound dressing, wherein the fluid comprises molecules with a protective coating; and an energy source configured to direct ultrasonic energy to the fluid and to degrade the protective coating and to activate a therapeutic property of the fluid.

2. The wound treatment system of claim 1, wherein the energy source is configured to activate a component of the fluid that degrades the protective coating.

3. The wound treatment system of claim 1, wherein the protective coating comprises a bioabsorbable glass.

4. The wound treatment system of claim 1, wherein the protective coating comprises a ceramic.

5. The wound treatment system of claim 1, wherein the energy source is configured to direct energy to the fluid proximal to the wound dressing.

6. The wound treatment system of claim 1, further comprising a conduit in fluid communication with the fluid storage device and the wound dressing.

7. The wound treatment system of claim 6, wherein the energy source is configured to direct energy to the fluid in the conduit.

8. The wound treatment system of claim 1, wherein the therapeutic property includes an anti-biotic property.

9. The wound treatment system of claim 1, wherein the therapeutic property includes an analgesic property.

10. The wound treatment system of claim 1, wherein the therapeutic property aids with debridement of tissue.

11. The wound treatment system of claim 1, wherein the therapeutic property improves the ability to remove the wound dressing from a wound.

12. The wound treatment system of claim 1, wherein the therapeutic property reduces biofilm buildup in a wound.

13. A method of treating a wound, the method comprising:
applying a wound dressing to the wound;
transporting fluid through a conduit to the wound dressing, wherein the fluid comprises molecules having a coating comprising an ultraviolet-activated protective material adapted to be partially broken down while traveling through the conduit; and
directing energy to the fluid proximal to the wound dressing to degrade the coating.

14. The method of claim 13, wherein degrading the coating activates a therapeutic property of the fluid.

15. The method of claim 14, wherein the therapeutic property includes an anti-biotic property.

16. The method of claim 14, wherein the therapeutic property includes an analgesic property.

17. The method of claim 14, wherein the therapeutic property aids with debridement of tissue.

18. The method of claim 14, wherein the therapeutic property improves the ability to remove the wound dressing from a wound.

19. The method of claim 14, wherein the therapeutic property reduces biofilm buildup in a wound.

20. A wound treatment system comprising:
a wound dressing;
a fluid storage device in fluid communication with the wound dressing;
a fluid comprising molecules with at least one type of therapeutic agent, wherein the molecules are constructed so that the therapeutic agent is inhibited by a light-sensitive branch which when broken thereby activates the therapeutic agent; and
an energy source configured to direct energy to the fluid and to control the light-sensitive branch of the molecules of the fluid.

21. The wound treatment system of claim 20, wherein the fluid comprises an anti-microbial agent.

22. The wound treatment system of claim 21, wherein the anti-microbial agent is hypochlorous acid (HOCl) or hypochlorite ion (ClO$^-$).

23. The wound treatment system of claim 20, wherein the fluid comprises molecules having an active agent that is a clotting agent.

24. The wound treatment system of claim 23, wherein the clotting agent is a trivalent salt, such as $Fe^{+++}$ or $Al^{+++}$.

25. The wound treatment system of claim 24, wherein the $Fe^{+++}$ compound is encapsulated in a glucose sensitive microcapsule, which increases in permeability to allow for the release of the $Fe^{+++}$ agent upon encountering glucose.

26. The wound treatment system of claim 20, wherein the fluid comprises multiple agents which are activated by different wavelengths of light or frequencies of energy.

* * * * *